United States Patent [19]
Nakano et al.

[11] Patent Number: 5,173,587
[45] Date of Patent: Dec. 22, 1992

[54] ELECTRIC HEATING APPLIANCE

[75] Inventors: Shigeru Nakano, Toyoshina; Kosaku Mitani, Osaka, both of Japan

[73] Assignees: Nihon Dennetsu Co., Ltd., Tokyo; Osaka Nishikawa Co., Ltd., Osaka, both of Japan

[21] Appl. No.: 837,702

[22] Filed: Feb. 19, 1992

Related U.S. Application Data

[63] Continuation of Ser. No. 630,478, Dec. 20, 1990, abandoned.

[30] Foreign Application Priority Data

Dec. 21, 1989 [JP] Japan .................. 1-329590

[51] Int. Cl.⁵ .......................... H05B 1/02; H05B 3/34
[52] U.S. Cl. .................... 219/212; 219/528; 307/127
[58] Field of Search ............... 219/211, 212, 529, 548, 219/549, 528; 307/127

[56] References Cited

U.S. PATENT DOCUMENTS

| | | | |
|---|---|---|---|
| 3,273,039 | 9/1966 | Godshalk | 307/127 |
| 3,313,960 | 4/1967 | Borys | 307/127 |
| 3,413,487 | 11/1968 | Gershen | 307/127 |
| 3,699,562 | 10/1972 | Kelly | 307/127 |
| 4,121,271 | 10/1978 | Tsai | 307/127 |
| 4,400,658 | 8/1983 | Yates | 307/127 |
| 4,492,878 | 1/1985 | Hamel | 307/127 |

Primary Examiner—Teresa J. Walberg
Attorney, Agent, or Firm—Nikaido, Marmelstein, Murray & Oram

[57] ABSTRACT

An electric heating appliance which is provided with a connecting terminal selecting circuit for the purpose of generating heat in an electric heater in a negative cycle of a commercial AC power source no matter which pole of a plug is connected to a grounding electrode of the power source when the plug is inserted into a plug socket of the power source, the connecting terminal selecting circuit consisting of a delay switch circuit adapted to insulate a heater circuit from the power source for a predetermined period of time when a power source switch is turned on, a heater potential detecting circuit adapted to detect the grounding electrode of the power source, and a change-over switch circuit adapted to connect the anode of an electric power controlling rectifying element for controlling the electric heater to the grounding electrode of the AC power source in accordance with an output signal from the heater potential detecting circuit.

2 Claims, 4 Drawing Sheets

ELECTRIC HEATING APPLIANCE

This application is a continuation of application Ser. No. 630,478 filed Dec. 20, 1990, now abandoned.

BACKGROUND OF THE INVENTION

1. Field of the Invention

This invention relates to an electric heating appliance, and more particularly, an electric heating appliance made so that the electric potential of a heater circuit becomes negative with respect to ground irrespective of the direction of insertion of a power source plug.

2. Description of the Prior Art

It has been known that, when an electrode kept at a negative potential is placed near a human body, a stiff shoulder healing effect can be obtained. Attempts to incorporate such a remedial appliance into an air-conditioner have heretofore been made.

For example, there are conventional techniques, which are disclosed in Japanese patent application Kokai publication No. 62-74373, for generating heat in a positive cycle of an AC power source, and insulating a heating circuit from the power source and providing this insulated heating circuit with negative electric potential in a negative cycle thereof. As shown in FIG. 4 of the accompanying drawings, the circuit disclosed in the above publication has a heater circuit consisting of an electric heater 1, an electric power controlling rectifying device 2 composed of SCR, and a temperature fuse 4, a main current circuit consisting of an insulating switch element (SCR) 8 for insulating the heater circuit from a commercial power source 6 in a negative cycle, and a diode 10, and a power source circuit for a control circuit 14, which consists of an insulating transformer 12, and the commercial power source 6 to which the insulating transformer is connected in parallel. The reference numeral 16 denotes a transformer for operating the insulating switch element 8 through the same transformer 16, a diode 17 and a resistor 18. The circuit of FIG. 4 is provided with a heat-sensitive layer 20 the impedance of which varies with temperature, and a signal line 22 for detecting the variations of impedance of this heat-sensitive layer 20, the signal line 22 being adapted to detect the temperature of the heat-sensitive layer 20 and apply a temperature signal to the control circuit 14 and a resistor 24 for melting the temperature fuse 4.

The condition of variations of electric potential in the case where a high-voltage generating circuit shown in the above publication is connected to the circuit of FIG. 4 will be described with reference to FIG. 5.

First, the circuit of FIG. 4, in which a grounding electrode E is connected as shown by a solid line, will be described. In this case, a circuit on the side of the anode of the electric power controlling rectifying element 2 is connected to the side of the grounding electrode, and the grounding electrode is set to zero volts. Consequently, in a negative cycle of the commercial power source, the insulating switch element 8 and electric power controlling rectifying element 2 are turned on, and, in a positive cycle thereof, the electric power controlling rectifying element 2 is turned off. The negative electric potential shown in the upper part of FIG. 5 is then supplied from a high negative electric potential generating circuit (not shown) connected to a cathode line in the negative electric potential insulating switch 8. In a negative cycle of the commercial power source 6, an electric current is supplied to the electric heater 1 to generate heat with the voltages at an a-portion of the electric heater 1, a central b-portion thereof and a c-portion thereof dropping to zero electric potential, negative electric potential of ½ of a peak level, and a peak negative electric potential, respectively, based on the ground potential.

When the electric power controlling element 2 is off, the grounding electrode E is set to zero volts. In the positive cycle of the commercial power source, the diode 10 stops the electric current, so that the electric current does not flow from the electric heater 1 to the grounding electrode E. Moreover, the insulating switch element 8 is turned off to insulate the electric heater 1 from the grounding electrode E. Accordingly, the electric potential of the electric heater 1 becomes negative. When a high negative potential is supplied, the level of the negative potential of the electric heater 1 becomes higher. In the negative cycle of the commercial power source with the electric power controlling rectifying element 2 off, the electric potential at all of the a, b and c-portions is zero. In accordance with the above statement, positive electric potential does not occur at all when the grounding electrode E is connected as shown by a solid line.

The case where a grounding electrode E' is connected as shown by a broken line in FIG. 4 unlike the above-described case will be described. In a positive cycle of the commercial power source with the grounding electrode E' set to zero volts, the insulating switch element 8 is turned on. When the electric power controlling rectifying element 2 is on, the voltages at the a, b and c-portions of the electric heater 1 drop to a peak positive electric potential, positive electric potential of ½ of the peak level, and zero electric potential, respectively, as shown in the lower portion of FIG. 5, to be heated. When the electric power controlling rectifying element 2 is off, positive electric potential of the same level occurs in all of the a, b and c-portions.

In a negative cycle of the commercial power source with the grounding electrode E' set to zero volts, the diode 10 stops the electric current, so that the electric current does not flow from the heater 1 to the grounding electrode E. Moreover, the insulating switch element 8 is turned off, so that the electric heater 1 is insulated from the commercial power source 6 with the electric potential thereof becoming negative.

As described above, when the grounding electrode E' is connected as shown by a broken line in FIG. 4, the electric potential of the electric heater 1 in a positive cycle of the commercial power source 6 becomes positive. Therefore, positive electric potential which is generally said to be harmful and useless to a human body works on the electric heater 1. Moreover, since a single-phase commercial AC power source does not have thereon any words about the grounded electrode, an ordinary man cannot use it with the direction of insertion of a power source plug limited.

SUMMARY OF THE INVENTION

The present invention has been developed in view of these problems. It is an object of the present invention to provide a heating appliance which contains means for automatically detecting the ground of an electric heater and constantly connecting a negative voltage generating circuit to the ground of the power source, and which is adapted to generate heat in a negative potential cycle on the basis of the grounding potential.

The electric heating appliance according to the present invention made for achieving this object has an electric heating circuit provided with a power source circuit, an electric power controlling rectifying element-carrying heater circuit and a connecting terminal selecting circuit for selecting polarity to be connected to the power source circuit and heater circuit, this connecting terminal selecting circuit consisting of a delay switch circuit to be now described, a heater potential detecting circuit adapted to detect the grounding electrode of the power source, and a change-over switch circuit.

The delay switch circuit consists of an insulating switch and a delay circuit. When the insulating switch is opened, the heater circuit is insulated from the power source circuit and the result of detection of occurrence of a leakage current by a stray capacitance, which has the heater circuit as one pole and the ground as the other, enables the detection of the anode circuit in the electric power controlling rectifying element in the heater circuit as to whether it is on the side of the grounding electrode. When the insulating switch is closed, the heater circuit is connected to the power source circuit. The delay circuit is operated so that, when the power source is connected to the power source circuit, a delay action is made to cause the insulating switch to be closed after the lapse of a predetermined period of time.

The delay means provided in the delay switch circuit may consist of a general delay circuit utilizing, for example, the charging time of a capacitor. It is not limited to such a delay circuit and a known delay means can also be used suitably.

The heater potential detecting circuit is adapted to detect the electric current flowing to the ground through one electrode of the power source circuit and heater circuit and determine whether this electrode is a grounding electrode of the power source or not.

The change-over switch circuit consists of a change-over switch for connecting the anode circuit of the electric power controlling rectifying element to the grounding electrode of the power source.

In the electric heating appliance according to the present invention, a voltage doubler circuit is provided in the above-mentioned circuit so as to enable the supplying of high negative potential when the heater circuit is insulated from the power source in a negative cycle of the electric power controlling rectifying element.

The electric heating appliance defined in the present invention means bedclothes to be heated, such as an electric blanket; an electric heating appliance, such as an electric carpet and an electric cushion; and thermal therapeutic apparatus.

DESCRIPTION OF THE PREFERRED EMBODIMENT

The electric heating appliance according to the present invention will now be described based on an embodiment thereof with reference to the accompanying further drawings.

Figure 1:
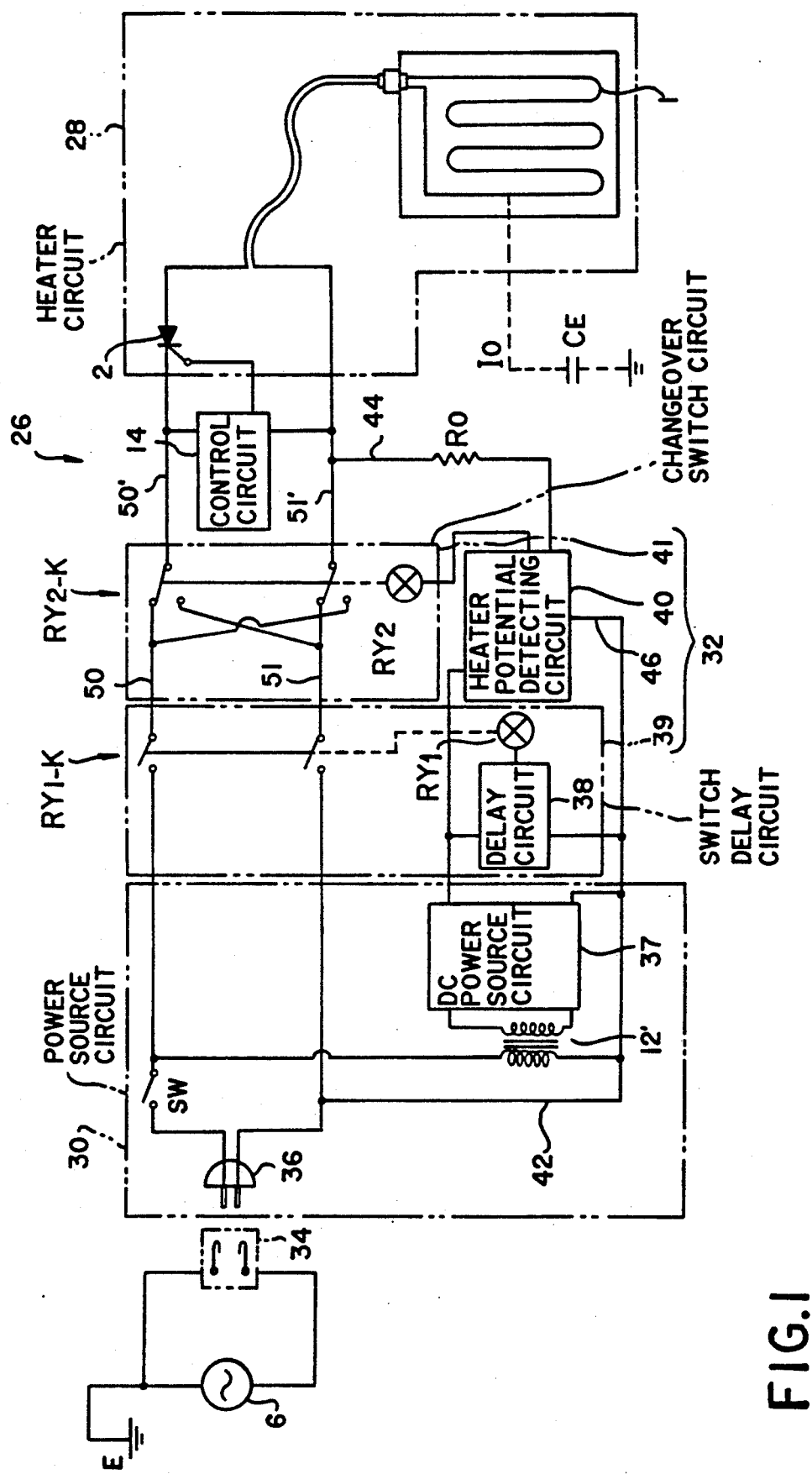
FIG. 1 is a circuit diagram of an embodiment of the heating appliance according to the present invention.

FIG. 1 is a block diagram for describing the outline and operation of the electric heating appliance of this embodiment. Referring to the drawing, an electric heating appliance 26 consists of a heater circuit 28 provided with an electric power controlling rectifying element 2, and a connecting terminal selecting circuit 32 provided between the heater circuit 28 and a power source circuit 30. A plug socket 34 constitutes a supply terminal of a commercial power source 6, and grounded E at its one electrode. The power source circuit 30 consists of a plug 36 to be connected to the plug socket 34, a transformer 12' constituting a power source for a main switch SW and the connecting terminal selecting circuit 32, and a DC power source circuit 37.

The connecting terminal selecting circuit 32 consists of a switch delay circuit 39 composed of a delay circuit 38, a relay circuit $RY_1$ driven by the delay circuit 38 and an insulating switch $RY_1$-K driven by the relay circuit $RY_1$, a heater potential detecting circuit 40, and a change-over switch circuit 41 composed of a relay circuit $RY_2$ driven by the heater potential detecting circuit 40 and a change-over switch $RY_2$-K driven, by the relay circuit $RY_2$-K. All of the relay circuits referred to above can also be formed with a non-contact circuit.

One power line of the power source 6 which is connected to electric heater 1 of the the heater circuit 28 and one line 42 of the power source circuit 30 is used as an electrode for detecting the ground line by the heater potential detecting circuit 40. Accordingly, the heater circuit 28 and heater potential detecting circuit 40 are connected by a line 44 in which a resistor $R_0$ is inserted, and the line 42 and heater potential detecting circuit 40 by a line 46.

The operation of the circuit of FIG. 1 will now be described. When the plug 36 is connected (as shown in the drawing) to the plug socket 34 with the main switch SW then closed, a power source current is supplied to the delay circuit 38 and heater potential detecting circuit 40. Consequently, the delay circuit 38 causes the heater potential detecting circuit 40 to make a ground line detecting action after the lapse of a predetermined period of time and until the insulating switch $RY_1$-K has been closed, i.e., until the electric power has been supplied to the heater circuit 28.

An heater potential detecting action is made by utilizing a stray capacitance $C_E$ formed by electric heater 1 of the heater circuit 28 and the ground E as shown in FIG. 1. When the plug 36 is inserted into the plug socket 34 as shown in the drawing, the lines 42, 46 are connected to a non-grounded portion of the power source. In the circuit of FIG. 1, an alternating current $I_0$ from the power source 6 flows through the stray capacitance $C_E$. Consequently, the heater potential detecting circuit 40 detects this flow of current to operate the change-over switch $R_2$-K (switch the illustrated state to the opposite state) so that the lines 50 and 51 are connected to the lines 51' and 50', respectively.

Conversely, when the plug 36 is inserted in an opposite manner into the plug socket to connect the line 42 of the power source circuit 30 to the ground E, the levels of the electric potential at both poles of the stray capacitance $C_E$ become equal, so that electric current does not flow. As a result, the heater potential detecting circuit 40 does not operate (illustrated state), and the change-over switch RY$_2$-K, and the lines 50, 50' and lines 51, 51' are left connected.

If the time constant of the delay circuit 38 is set to a suitable level, the insulating switch RY$_1$-K is closed after the completion of this switching action (including some cases where a switching action is not made) to enable a power source current to be supplied to the heater circuit 36. Therefore, when the plug 36 is inserted unintentionally into the plug socket 34, the connecting terminal selecting circuit 32 constantly connects the anode circuit of the electric power controlling rectifying element 2 to ground E.

The principal portion of the circuit of FIG. 1 will now be described with reference to FIG. 2. The circuit of FIG. 2 is provided with a high negative potential-supplying voltage doubler circuit 48.

Figure 2:
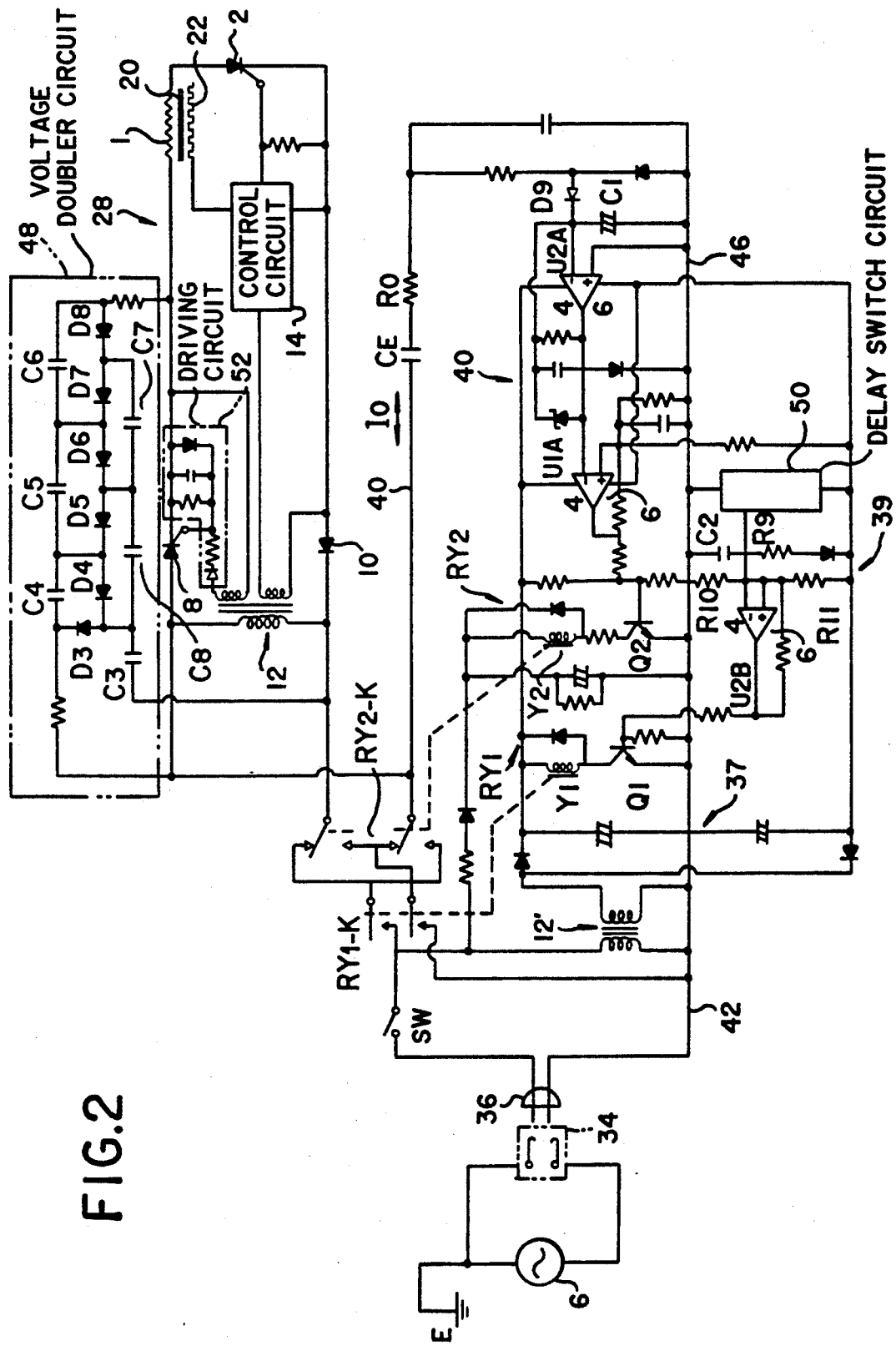
FIG. 2 is a diagram of a grounding electrode detecting circuit in the embodiment of FIG. 1.

Referring to FIG. 2, in the heater potential detecting circuit 40, the alternating current $I_0$ through the stray capacitance $C_E$ shown in FIG. 1 is rectified by a diode D$_9$, integrated by an OP amplifier U2A and sent out as a DC signal, and a signal of what is thus detected is input into an OP amplifier U1A to obtain a control signal to be output to the relay circuit RY$_2$. A solenoid Y$_2$ in the relay circuit RY$_2$ operates the change-over switch RY$_2$-K (including some cases where it is not operated) in accordance with the ON- and OFF-state of a transistor Q$_2$, which is operated by this control signal, to connect the ground line of the power source 6 to the anode circuit of the electric power controlling rectifying element 2.

In the delay switch circuit 39, the voltage variation, which is determined by the time constants of the capacitor C$_2$ and resistor R$_9$, and the partial potential levels in the resistors R$_{10}$, R$_{11}$ are compared in the OP amplifier U2B after the main switch SW is closed, and the charging of the capacitor C$_2$ progresses. A decrease of the voltage occurring in the resistor R$_9$ is detected to operate the transistor Q$_1$, close the insulating switch RY$_1$-K and supply a power source current to the heater circuit 28. A discharge circuit 50 consists of a switch circuit adapted to discharge the capacitor C$_2$ when the power source is cut off, and initialize and operate the delay switch circuit 39. Accordingly, even when the main switch SW is closed again immediately after the power source is cut off, the connecting terminal selecting circuit 32 can be actuated immediately.

The voltage doubler circuit 48 consists of an ordinary voltage doubler circuit cascade-connected by using capacitors C$_3$-C$_8$ and diodes D$_3$-D$_8$. In the case of the voltage doubler circuit shown in the drawing, a high voltage of 600 V occurs, and negative electric potential of this voltage is supplied to the heater circuit 28. Therefore, when the electric current flowing in the electric heater 1 in a negative cycle of the electric power, controlling rectifying element 2 is cut off, the heater circuit 28 is insulated from the power source by the insulating switch element 8 and diode 10, whereby high negative potential can be supplied thereto.

Figure 4:
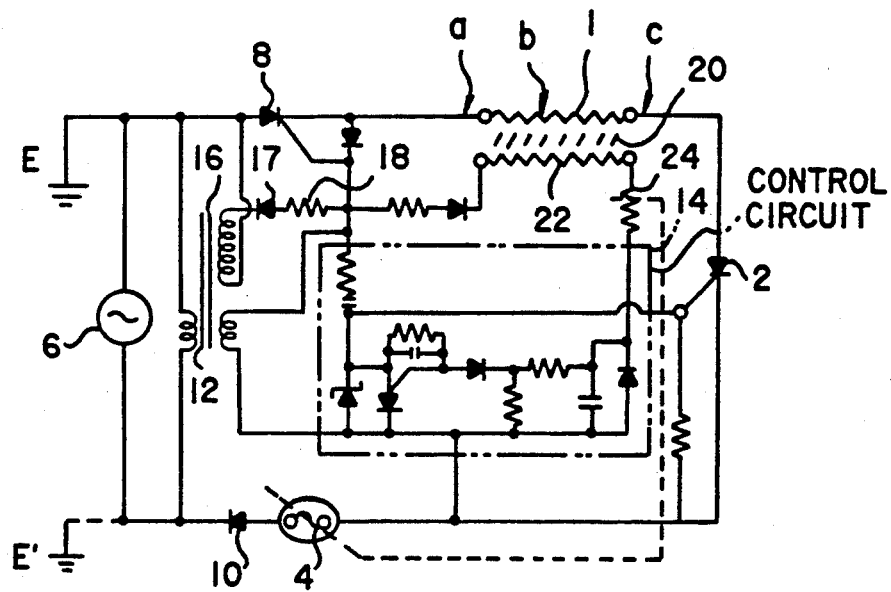
FIG. 4 is a circuit diagram of a conventional heating appliance.
Figure 5:
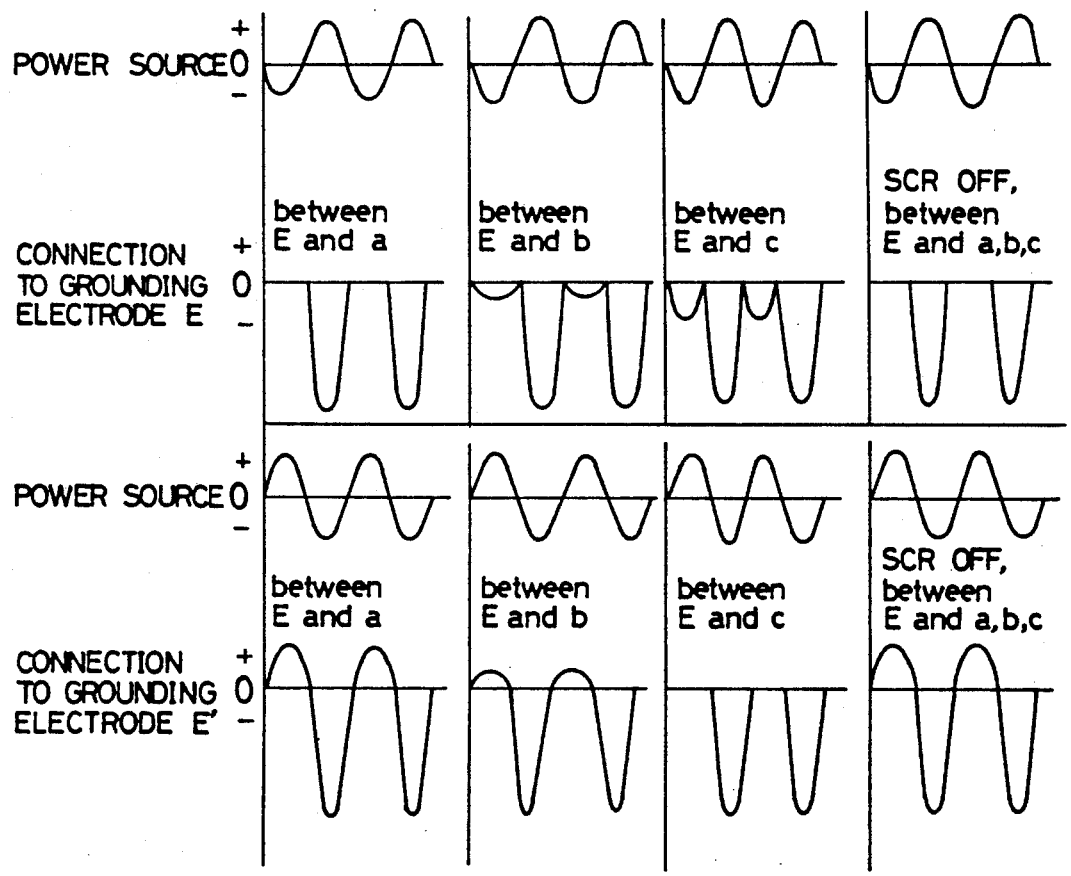
FIG. 5 is a graph showing the operational condition of the conventional circuit shown in FIG. 4, and illustrating the problems.

Referring to FIG. 2, a circuit 52 is a driving circuit for the insulating switch element 8, and the control circuit 14 consists of the same control circuit 14 as shown in FIG. 4, a description of the details of this control circuit being therefore omitted. In order to prevent the diagram of FIG. 2 from being complicated, the illustrations of fuse melting means, which is used when the temperature increases excessively, noise eliminating means and various other kinds of safety means are omitted.

Figure 3:
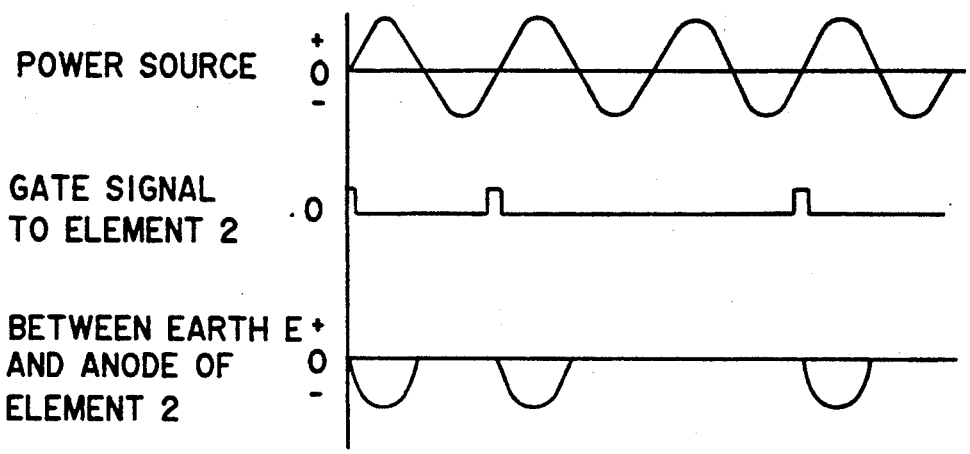
FIG. 3 is a graph illustrating the operational condition of the circuit of FIG. 1.

FIG. 3 is a graph illustrating the operation of the circuit of FIG. 1. Referring to the drawing, when the power source is connected to the electric heating appliance 26, electric current is supplied as shown in FIG. 3 to the electric heater 1 through the electric power controlling rectifying element 2 in a positive cycle of the power source 6 no matter which line of the power source circuit 30 is connected to the ground line of the power source 6. Consequently, a voltage drop of negative potential with respect to the ground occurs, and heat is generated. When the temperature is high, the electric power controlling rectifying element 2 is operated by the control circuit 14, and the electric current flowing to the electric heater 1 is cut off. Since a voltage drop does not then occur in the electric heater 1, the electric potential of ground and electric heater 1 as a whole becomes equal, i.e., zero. Therefore, when an electric current is supplied to the electric heater 1, negative potential with respect to ground occurs, and, in the other case, the electric potential of the electric heater becomes zero. Accordingly, the harmful and useless positive potential does not occur at all.

Thus, the electric heating appliance according to the present invention is provided with grounding electrode detecting means and capable of automatically connecting ground of a power source to the anode circuit of an electric power controlling rectifying element. Accordingly, while the heating appliance is used, heat is generated on the negative potential side with respect to the ground to enable the therapeutic and health promoting effect based on the negative potential to be provided simultaneously with the generation of heat.

What is claimed is:

1. An electric heating appliance including a negative potential generating circuit for feeding negative potential to an electric heater, said electric heating appliance comprising:

a power source circuit to be connected to an alternate current power source;

a heater circuit including the electric heater provided at a downstream position of a power controlling rectifying element in a flow direction of current; and a connection selecting circuit, provided between the power source circuit and the heater circuit for selective connection of terminals, said connecting selecting circuit including a potential detecting circuit for detecting current flow from one terminal of the power source circuit to ground through the electric heater and for detecting whether or not a potential of the electric heater is on a ground side, a change-over switch circuit controlled by a control signal produced by said potential detecting circuit and connecting an anode terminal of the power controlling rectifying element to a grounding terminal of said alternate current power source, and a delay switch circuit including a delay circuit and an insulating switch operated by the delay circuit, wherein when the power source circuit is connected to the alternate current power source and after the potential of the electric heater is detected by the potential detecting circuit, said delay switch circuit connecting the power source circuit to the change-over switch circuit.

2. The electric heating appliance according to claim 1, wherein a voltage doubler circuit is provided between the connection selecting circuit and the heater circuit, for amplifying negative potential to be fed to the heater circuit.

* * * * *